(12) United States Patent
Jautelat et al.

(10) Patent No.: US 6,472,560 B2
(45) Date of Patent: Oct. 29, 2002

(54) PROCESS FOR PREPARING HYDRAZODICARBONAMIDE VIA KETIMINES

(75) Inventors: Manfred Jautelat, Burscheid (DE); Walter Leidinger, Düsseldorf (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/906,356

(22) Filed: Jul. 16, 2001

(65) Prior Publication Data

US 2002/0013495 A1 Jan. 31, 2002

(30) Foreign Application Priority Data

Jul. 19, 2000 (DE) ......................... 100 35 010

(51) Int. Cl.[7] ............................... C07C 28/00
(52) U.S. Cl. ..................................... 564/35
(58) Field of Search ....................... 564/35, 249, 34

(56) References Cited

U.S. PATENT DOCUMENTS 3,969,466 A * 7/1976 Brown et al.
3,978,049 A * 8/1976 Schirmann et al.
4,049,712 A * 9/1977 Schirmann et al.
4,176,135 A 11/1979 Ohno et al. ................. 260/554

FOREIGN PATENT DOCUMENTS

GB 1146233 3/1969

OTHER PUBLICATIONS

CA:89:163091 ab of JP53063315 Jun. 1978.*
CA:69:26817 ab of SU201422 Oct. 1967.*
CA:81:13069 abs of Report (1972) ICT–8/72 44 pages available from Govt. Rep. Announce. (U.S.) 74(5) 57 report 1974.*
Catal. Rev.–Sci. Eng., 32(3), (month unavailable) 1990, pp. 229–277, H. Hayashi, "Hydrazine Synthesis by a Catalytic Oxidation Process".
Ullmann's Encyclopedia of Industrial Chemistry, vol. A13 (date unavailable), pp. 179–185.

* cited by examiner

Primary Examiner—Jean F. Vollano
(74) Attorney, Agent, or Firm—Joseph C. Gill; Richard E.L. Henderson

(57) ABSTRACT

The present invention relates to a novel process for preparing hydrazodicarbonamide (HDC) that is, after oxidation to azodicarbonamide (ADC), used industrially as a polymer auxiliary.

9 Claims, 1 Drawing Sheet

PROCESS FOR PREPARING HYDRAZODICARBONAMIDE VIA KETIMINES

BACKGROUND OF THE INVENTION

The present invention relates to a novel process for preparing hydrazodicarbonamide ("HDC") which is, after oxidation to azodicarbonamide ("ADC"), used as a polymerization auxiliary (Ullmann's Encyclopaedia of Industrial Chemistry, Vol. A13, 185).

It is generally known that HDC is obtained from the reaction of hydrazine with urea (Ullmann's Encyclopaedia of Industrial Chemistry, Vol. A13, 185). The yields in this process are good. However, hydrazine is relatively expensive since it is prepared by chlorination of ammonia and is also classified as a hazardous substance.

It is also known that hydrazine can be obtained from the reaction of ammonia and hydrogen peroxide in the presence of ketones and catalysts. However, the yields leave something to be desired. (Ullmann's Encyclopaedia of Industrial Chemistry, Vol. A13, 182).

Furthermore, it is known that benzophenonimine can be oxidized using oxygen in the presence of catalysts to give benzophenonazine, however, which can be cleaved only with strong acids such as sulfuric acid to form hydrazinium sulfate (Catal. Rev. CR Sci. Eng., 1990, 32, 229–277). The direct reaction of this benzophenonazine with urea to form HDC is, however, not successful.

SUMMARY OF THE INVENTION

It has now been found that hydrazodicarbonamide ("HDC") of formula (I)

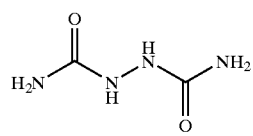

(I)

can be prepared by a process comprising (a) reacting aliphatic ketones of formula (II)

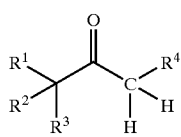

(II)

wherein
$R^1$, $R^2$, and $R^3$ are identical or different and are each substituted or unsubstituted alkyl, and
$R^4$ is hydrogen, substituted or unsubstituted alkyl, or substituted or unsubstituted cycloalkyl, or
$R^1$ together with $R^2$ or $R^4$ form an alkylene chain, with ammonia under pressure to form ketimines of formula (III)

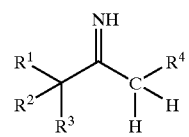

(III)

wherein
$R^1$, $R^2$, $R^3$ and $R^4$ are as defined above, (b) oxidizing the ketimines of formula (III) with oxygen in the presence of catalysts to form ketazines of formula (IV)

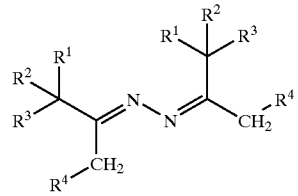

(IV)

wherein
$R^1$, $R^2$, $R^3$ and $R^4$ are as defined above, and (c) reacting the ketazines of formula (IV) with urea and water in the presence of catalysts.

DETAILED DESCRIPTION OF THE INVENTION

Figure 1:
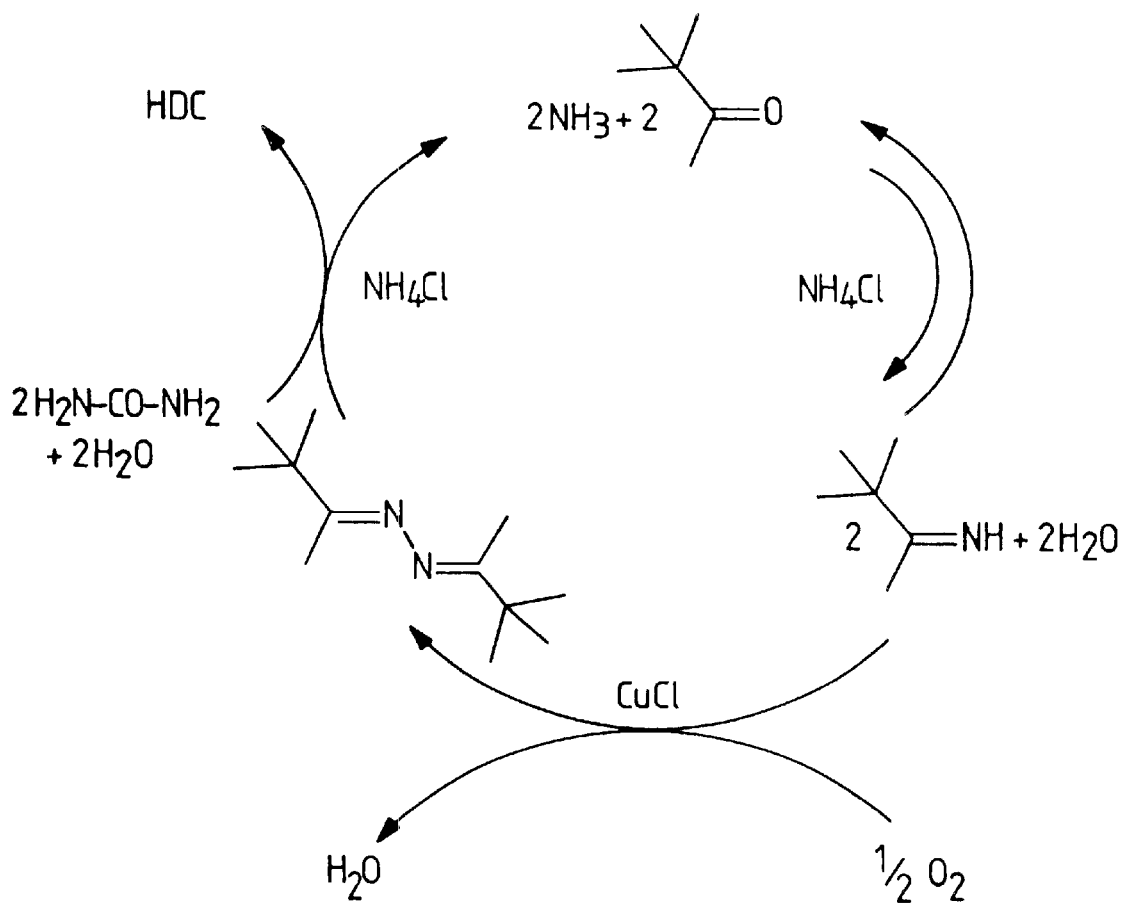
FIG. 1 illustrates an embodiment of the invention using 3,3-dimethyl-2-butanone (pinacolone) as starting ketone.

It is extremely surprising that aliphatic ketimines of formula (III) are formed with high selectivity and can be oxidized with high selectivity using oxygen to form ketazines of formula (IV). It is likewise surprising that the ketazines of formula (IV) can be reacted directly with urea and water to give hydrazodicarbonamide (I).

The process of the invention has a series of advantages. Thus, the use of hydrazine can be avoided, oxygen is used in place of chlorine as oxidant, and the ketone is set free in the last step and can be returned to the cyclic process. The net reaction of the cyclic process is the oxidation of urea using oxygen to give hydrazodicarbonamide and water.

If 3,3-dimethyl-2-butanone (i.e., pinacolone) is used as starting ketone, the cyclic process according to the invention can be illustrated by Scheme 1.

The ketones used for carrying out the process of the invention are defined in general terms by the formula (II). Preference is given to compounds of formula (II) in which
$R^1$, $R^2$, and $R^3$ are identical or different and are each straight-chain or branched alkyl having from 1 to 6 carbon atoms,
$R^4$ is hydrogen, straight-chain or branched alkyl having from 1 to 6 carbon atoms, or cycloalkyl having from 3 to 6 carbon atoms, where these radicals may bear one or two identical or different substituents selected from among halogen, alkoxy having from 1 to 4 carbon atoms, and cycloalkyl having from 3 to 6 carbon atoms, or
$R^1$ together with $R^2$ or $R^4$ form an alkylene chain having from 2 to 6 carbon atoms, where this chain may bear from 1 to 4 identical or different substituents selected from among halogen, alkyl having from 1 to 4 carbon atoms, and cycloalkyl having from 3 to 6 carbon atoms.

Particular preference is given to using as starting materials ketones of formula (II) in which $R^1$, $R^2$, and $R^3$ are identical or different and are each methyl or ethyl, and $R^4$ is hydrogen, methyl, ethyl, isopropyl, or tert-butyl, or $R^1$ and $R^2$ together form an alkylene chain having 4 or 5 carbon atoms, or $R^1$ and $R^4$ together form an alkylene chain having 3 or 4 carbon atoms.

The ketones of formula (II) are known or can be prepared by known methods.

Step (a) of the process of the invention is carried out using ammonia under a pressure (either its own pressure or inert gas pressure) of from 20 to 300 hectopascals, preferably from 50 to 200 hectopascals. Ammonia is used in a molar ratio to the ketone of from 1:1 to 20:1, preferably from 2:1 to 10:1. In addition, a catalyst, preferably ammonium salts such as ammonium chloride or ammonium sulfate, can be used if desired.

Suitable diluents are all inert solvents. Preference is given to carrying out the reaction without diluents.

The reaction temperatures when carrying out step (a) can be varied within a certain range. In general, temperatures of from 0° C. to 200° C. (preferably from 20° C. to 120° C.) are employed.

Since the ketimine of formula (III) that is obtainable as intermediate is readily hydrolyzed, the reaction mixture is cooled to temperatures of from 20° C. to −78° C. (preferably from 0° C. to −30° C.) before depressurization. The organic phase is separated from the aqueous phase and can be purified after drying. The mixture of ketimine of formula (III) and the starting material of formula (II) is advantageously used directly in the reaction step (b) without further purification.

The ketimine of formula (III) is used in reaction step (b) either in pure form or in admixture with the ketone of formula (II). Oxygen can be used in pure form or diluted with inert gases such as nitrogen, preferably as air, under atmospheric pressure or under a pressure of up to 20 hectopascals.

Suitable catalysts are salts of the metals Cr, Mn, Fe, Co, Ni, Tl, Pb, Cu, or Ag, preferably their halides, particularly preferably copper derivatives such as CuCl or CuBr. The catalysts can be used alone, in aqueous solution, in mixtures of various metal salts, or applied to a support. In general, the catalyst is used in amounts of from 0.01 to 30% by weight, preferably from 0.05 to 20% by weight.

Suitable diluents are all inert solvents. Unreacted ketone of formula (II) from reaction step (b) is preferably employed.

The reaction temperatures when carrying out step (b) can be varied within a certain range. In general, temperatures of from 0° C. to 100° C. (preferably from 20° C. to 80° C.) are employed.

To bind the water formed in the oxidation, it is advantageous to use a desiccant such as zeolite or sodium sulfate.

For the work-up, the organic phase is separated from the aqueous catalyst phase and purified by distillation. The isolated ketone of formula (II) is returned to the circuit, the catalyst solution is likewise reused directly or after work-up and the ketimine of formula (IV) is used in step (c).

In reaction step (c) of the process of the invention, the ketazine of formula (IV) is reacted with urea and water in the presence of a catalyst. Ketazine and urea are used in a molar ratio of from 1:2 to 1:5, preferably from 1:2 to 1:3. Water is used as solvent in an equimolar amount or in a large excess.

Suitable catalysts are mineral acids such as sulfuric acid or phosphoric acid, organic acids such as trifluoroacetic acid or trifluoromethanesulfonic acid, or acid salts such as ammonia sulfate or ammonium chloride. These catalysts can be used in catalytic amounts of 0.1% by weight and more or in a large excess.

Suitable diluents are polar solvents such as dimethylformamide ("DMF"), acetic acid, water, or mixtures thereof.

The reaction temperatures when carrying out step (c) can be varied within a certain range. In general, temperatures of from 80° C. to 150° C. (preferably from 100° C. to 130° C.) are employed.

The reaction can be carried out at atmospheric pressure or under pressure, with the removal of the ammonia liberated having to be ensured.

The reaction product hydrazodicarbonamide of formula (I) can be isolated from the reaction solution as a solid product by filtration with suction. The ketone of formula (II) that is set free is isolated from the reaction solution by distillation and returned to the cyclic process.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

Preparative Example a) Pinacolonimine: 50 g (0.5 mol) of 3,3-dimethyl-2-butanone (pinacolone) and 0.5 g of ammonium chloride were placed in a 0.3 liter autoclave, 100 ml (4 mol) of liquid ammonia were subsequently added, and the mixture was heated to 80° C. The pressure was increased to 200 bar using nitrogen. The mixture was then stirred for 2 hours at 80° C. After the reaction was cooled to 0° C., the pressure was slowly released. The reaction mixture was poured into a separating funnel and the phases are separated.

Aqueous phase (bottom, having a high $NH_3$ content): 5.77 g

Organic phase (top): 49.29 g (0.3 mol, 60% imine); GC: 37.0% ketone and 62.6% pinacolonimine; $^1$H-NMR ($CDCl_3$, 400 MHz): δ1.15 (9H, s); 2.03 (3H, s); ~9.0 (NH); GC/MS(CI): 100 ($M+H^+$)

b) Pinacolonazine: 5.0 g of a mixture of pinacolonimine (24.6%, 12.4 mmol) in 3,3-dimethyl-2-butanone (pinacolone) together with 0.2 g of copper(I) chloride and 2.0 g of Zeolith 134® were placed in a reaction vessel at room temperature. While passing air over the mixture and stirring, the mixture was subsequently heated at 40° C. for 5 hours. After cooling, the reaction mixture was diluted with dichloromethane and shaken with dilute ammonia solution. The organic phase was dried over sodium sulfate, filtered, and evaporated under reduced pressure to give 1.0 g (4.7 mmol, 76% of theory) of pinacolonazine having a GC content of 93.4% and 2.5% of pinacolone. $^1$H-NMR ($CDCl_3$, 400 MHz): δ1.17 (18H, s); 1.68 (6H, s); GC/MS(EI): 196 ($M^+$).

c) Hydrazodicarbonamide (HDC): 6.2 g of ammonium sulfate were added to a mixture of 1.96 g (10 mmol) of pinacolonazine with 3.6 g (60 mmol) of urea in 5 ml of water and 5 ml of DMF and the reaction mixture was heated at reflux over the weekend (72 h). The product that precipitated was filtered off with suction, washed with water, and dried under reduced pressure to give 1.0 g (8.5 mmol, 85%) of HDC having a melting point of 254° (decomposition).

What is claimed is:

1. A process for preparing hydrazodicarbonamide of formula (I)

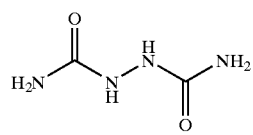

(I)

comprising (a) reacting an aliphatic ketone of formula (II)

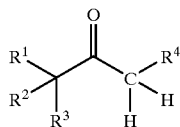

(II)

wherein $R^1$, $R^2$, and $R^3$ are identical or different and are each substituted or unsubstituted alkyl, and $R^4$ is hydrogen, substituted or unsubstituted alkyl, or substituted or unsubstituted cycloalkyl, or $R^1$ together with $R^2$ or $R^4$ form an alkylene chain, with ammonia under pressure to form a ketimine of formula (III)

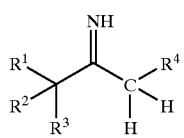

(III)

wherein $R^1$, $R^2$, $R^3$ and $R^4$ are as defined above, (b) oxidizing the ketimine of formula (III) with oxygen in the presence of a salt of Cr, Mn, Fe, Co, Ni, Tl, Pb, Cu or Ag as catalyst to form a ketazine of formula (IV)

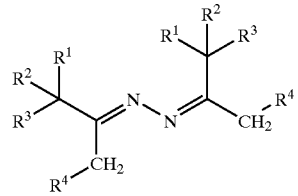

(IV)

wherein $R^1$, $R^2$, $R^3$ and $R^4$ are as defined above, and (c) reacting the ketazine of formula (IV) with urea and water in the presence of a catalyst.

2. A process according to claim 1 wherein, in the compound of formula (II), $R^1$, $R^2$, and $R^3$ are identical or different and are eah straight-chain or branched alkyl having from 1 to 6 carbon atoms, $R^4$ is hydrogen, straight-chain or branched alkyl having from 1 to 6 carbon atoms, or cycloalkyl having from 3 to 6 carbon atoms, where these radicals optionally bear one or two identical or different substituents selected from among halogen, alkoxy having from 1 to 4 carbon atoms, and cycloalkyl having from 3 to 6 carbon atoms, or $R^1$ together with $R^2$ or $R^4$ form an alkylene chain having from 2 to 6 carbon atoms, where this chain optionally bears from 1 to 4 identical or different substituents selected from among halogen, alkyl having from 1 to 4 carbon atoms, and cycloalkyl having from 3 to 6 carbon atoms.

3. A process according to claim 1 wherein in step (a) ammonia is used under a pressure of from 20 to 300 hectopascals and the reaction temperature is from 0° C. to 200° C.

4. A process according to claim 1 wherein the reaction mixture from step (a) is cooled to temperatures of from 20° C. to −78° C. before any subsequent release of pressure.

5. A process according to claim 1 wherein in reaction step (b) oxygen is used in pure form or is diluted with an inert gas at atmospheric pressure or under a pressure of up to 20 hetopascals.

6. A process according to claim 1 wherein the reaction temperature in step (b) is from 0° C. to 100° C.

7. A process according to claim 1 wherein in step (c) the molar ratio of the ketazine of formula (IV) to urea is from 1:2 to 1:5.

8. A process according to claim 1 wherein in step (c) the catalyst is used in amounts of at least 0.1 % by weight or in a large excess.

9. A process according to claim 1 wherein the reaction temperature in step (c) is from 80° C. to 150° C.

* * * * *